United States Patent
Bollenbeck et al.

(10) Patent No.: US 10,617,298 B2
(45) Date of Patent: Apr. 14, 2020

(54) MAGNETIC RESONANCE DEVICE, PATIENT SUPPORT AND METHOD FOR DATA TRANSMISSION USING A CONNECTING DEVICE FOR ESTABLISHING A DATA LINK BETWEEN A DOCKING DEVICE AND A PATIENT SUPPORT

(71) Applicant: Siemens Healthcare GmbH, Erlangen (DE)

(72) Inventors: Jan Bollenbeck, Eggolsheim (DE); Robert Rehner, Neunkirchen am Brand (DE)

(73) Assignee: Siemens Healthcare GmbH, Erlangen (DE)

( * ) Notice: Subject to any disclaimer, the term of this patent is extended or adjusted under 35 U.S.C. 154(b) by 314 days.

(21) Appl. No.: 15/581,988

(22) Filed: Apr. 28, 2017

(65) Prior Publication Data
US 2017/0311802 A1 Nov. 2, 2017

(30) Foreign Application Priority Data

Apr. 28, 2016 (DE) .................. 10 2016 207 267

(51) Int. Cl.
*A61B 5/00* (2006.01)
*H04W 4/80* (2018.01)
*A61B 5/055* (2006.01)

(52) U.S. Cl.
CPC ............ *A61B 5/002* (2013.01); *A61B 5/0017* (2013.01); *A61B 5/0555* (2013.01); *H04W 4/80* (2018.02)

(58) Field of Classification Search
CPC ...... A61B 5/0017; A61B 5/0555; H04W 4/80
See application file for complete search history.

(56) References Cited

U.S. PATENT DOCUMENTS

| | | | |
|---|---|---|---|
| 5,525,905 A | 6/1996 | Mohapatra et al. | |
| 7,173,426 B1* | 2/2007 | Bulumulla | G01R 33/3415 324/318 |
| 2002/0179092 A1 | 12/2002 | Swennen et al. | |
| 2007/0096739 A1* | 5/2007 | Nakabayashi | G01R 33/3415 324/318 |
| 2009/0137898 A1 | 5/2009 | Demharter et al. | |
| 2009/0315556 A1* | 12/2009 | Driemel | G01R 33/3415 324/307 |
| 2010/0072997 A1 | 3/2010 | Fischer et al. | |

(Continued)

OTHER PUBLICATIONS

Transfer Jet Whitepaper, "Worlds are About to Touch," Rev. 1.2, TransferJet Consortium, pp. 1-11 (Sep. 2015).

(Continued)

*Primary Examiner* — Baisakhi Roy
*Assistant Examiner* — Jason M Ip
(74) *Attorney, Agent, or Firm* — Schiff Hardin LLP

(57) ABSTRACT

A connecting device for establishing a data link between a docking device provided at a part of a magnetic resonance scanner, and a patient support, with at least one slot for a local coil, which can be docked to the docking device, has a first data transmission device on the patient support side, which interacts with a second data transmission device on the docking device side in order to establish the data link in the docked state. The data transmission devices each have at least one communication device designed for wireless near field communication.

16 Claims, 2 Drawing Sheets

(56) References Cited

U.S. PATENT DOCUMENTS

2012/0117730 A1* 5/2012 Lemire ................ A61G 1/0268
5/611
2015/0087966 A1 3/2015 Anderson et al.

OTHER PUBLICATIONS

TransferJet Overview, "Concept and Technology," Rev. 1.5, TransferJet Consortium, pp. 1-45 (Aug. 2015).
TransferJet Wikipedia article (2013).

* cited by examiner

MAGNETIC RESONANCE DEVICE, PATIENT SUPPORT AND METHOD FOR DATA TRANSMISSION USING A CONNECTING DEVICE FOR ESTABLISHING A DATA LINK BETWEEN A DOCKING DEVICE AND A PATIENT SUPPORT

BACKGROUND OF THE INVENTION

Field of the Invention

The invention relates to a connecting device for establishing a data link between a patient support and a docking device provided on a part of a magnetic resonance scanner, to which the patient support can be docked, the patient support having at least one slot for a local coil, and the connecting device having a first transmission device at the patient support, which interacts with a second data transmission device, at the docking device, for establishing the data link in the docked state. The invention also relates to a magnetic resonance apparatus having a scanner, a patient support and a method for data transmission that are designed to implement such a method.

Description of the Prior Art

Local coils that are to be positioned as close as possible to the area of a patient to be imaged are frequently used in magnetic resonance imaging, in order to achieve an improved signal-to-noise ratio and further advantages. For this purpose, patient supports, in particular the table thereof on which the patient lies, in modern magnetic resonance apparatuses in most cases have slots, into which a coil connector of a local coil can be inserted in order to allow a data transmission from the local coil to the magnetic resonance apparatus, and if applicable vice versa. Magnetic resonance signals received by the local coil are thus able to be transmitted to a receiving device of the magnetic resonance apparatus. To this end, an optical cable link between the patient support and the receiving device can be established.

In order to enable an improved workflow and/or an improved transport of patients, patient supports have been proposed that can be separated from the magnetic resonance scanner of the apparatus, in order, for instance, to be loaded with the patient while another patient on another patient support is being examined. In order to be able to once again arrange the patient support at the magnetic resonance device, the latter has a docking device, that includes a holder for instance, into which the patient support is slid. Even with dockable patient supports of this type, a data transmission must be possible at least from local coils to the receiving device of the magnetic resonance device. A plug-in connection, which interacts with a corresponding plug-in connector of the dockable patient support, is consequently typically provided as part of the docking device. The electrical connection to the magnetic resonance apparatus is achieved by a docking point of this type, which can be positioned variably.

The plug-in connection device used in the prior art has a number of coaxial plug-in connections for transmitting magnetic resonance signals and various direct current contacts for energy transmission and communication purposes. Since a patient support is to be docked and undocked frequently, a large number of mating cycles is to be expected, so that the plug-in connection device can be designed for 30,000 mating cycles or more for instance. The interface provided as the plug-in connection device also makes a high demand on the precision of the docking process, in order that the contacts can be neatly plugged and connected and there is no increased wear or even distortion of the metal contacts. Since the contacts are occasionally exposed, they may also become soiled.

It was also known to optically convert the magnetic resonance signals already in the patient support, such as in the table, into optical signals that are transmitted via an optical interface, namely an optical cable link, to the magnetic resonance apparatus, specifically to a receiving device thereof. The disadvantages of the position accuracy demand, the mating cycles and the soiling also occur with this solution.

US 2015/0087966 A1 discloses a method of communication between a magnetic resonance control system and radio frequency coils using a new mechanical concept, wherein the data transmission from the local coil to the patient table is carried out using near field communication (NFC), for instance using TransferJet technology.

SUMMARY OF THE INVENTION

An object of the invention is to provide for docking a patient support to a docking device with reduced demands on the position accuracy and the protection against soiling, as well as with increased robustness.

To achieve this object, by a connecting device in accordance with the invention of the general type noted above, but wherein the data transmission devices each have at least one communication device designed for wireless near field communication.

Thus in accordance with the invention, at least one first communication device is provided at the first data transmission device and at least one second communication device is provided at the second data transmission device. A data link can be set up between each pair of first and second communication devices, via which data to be transmitted can be transferred from the patient support to a control computer of the magnetic resonance apparatus, in particular a receiving device, or vice versa. This means that the data link is designed for bidirectional communication. In accordance with the invention, it is thus possible to completely dispense with galvanic or optical links for data transmission purposes. Instead, it is provided to transmit the data, particularly already-digitized data such as magnetic resonance signals, via each near field coupling, as a near field communication between the docking device and the patient support. Such an interface formed by near field communication allows data to be transmitted wirelessly over a distance of a few cm.

It is thus possible to structurally design the connecting device such as to permit the docking connection to be closed on both sides, in other words at the patient support and at the docking device, without open galvanic and/or optical contacts. It is even possible to provide or allow air gaps between the patient support and the docking device in the data transmission range.

A number of advantages are thus achieved. The demand with respect to position accuracy on the data interface is reduced. Demands with respect to the number of mating cycles can be easily realized with a wireless interface of this type. The interface is also not susceptible to soiling, since it can be a closed structure. Many specific technologies in near field communication manage with minimal transmitting powers, thus avoiding affecting the image quality. The communication devices can be cost-effectively obtained as very small modules and easily installed.

It should be noted that the communication devices do not necessarily have to be designed as a transmitting device and receiving device in each case; instead it is conceivable, dependent on the desired data transmission device, for the corresponding pair of first and second communication devices to have a communication device functioning solely as a transmitting device (TX), and the other functioning solely as a receiving device (RX). If magnetic resonance signals are only to be transmitted from the patient support to the docking device via a pair of first and second communication devices for instance, the first communication device of the first data transmission device can be designed as a transmitting device, the second communication device of the second data transmission device as a receiving device. It may be expedient, however, to design both communication devices as transmitting and receiving devices for at least one pair of communication devices, in particular a pair of communication devices assigned to the transmission of control signals and/or control information.

In an embodiment, the communication devices are NFC devices and/or TransferJet devices. TransferJet is a novel wireless near field communication technology that allows data to be transmitted at very high speed in one or both directions using corresponding coupling antennae between two communication devices arranged close to one another. The range of coverage realistically amounts to just a few cm. Other variants of the near field communication can naturally also be applied within the scope of the present invention.

In general, the communication range of the communication devices amounts to less than 10 cm, in particular less than 5 cm. These are typical communication ranges for near field communications. Within the scope of the present invention, however, even shorter communication ranges are conceivable, for instance communication ranges of at most 3 cm, in order to minimize possible interference with the imaging.

The data link can be designed to transmit digitized reception signals received by a local coil on the patient support, and/or digital coil information about a local coil inserted into a slot, and/or control signals of the magnetic resonance apparatus to a local coil. Aside from magnetic resonance signals (reception signals), it is thus also possible via the described interface to transmit further data, for instance control signals and/or further information, in particular coil information such as coil codes and the like, which are typically read out at the slots of the table of the patient support.

For the digitization of reception signals of a local coil, the first data transmission device can have at least one analog-digital converter for digitizing data to be transmitted via the data link. Digitization in the docking point itself is thus possible. It may be preferable, however, to install the analog-digital converter alternatively in the patient support, in particular close to a slot for the local coil and/or as part of this slot. This is advantageous because the signal transmission can be carried out optically-digitally via optical fibers within the table of the patient support and so no sheath current filters are required. Costs and installation space are saved in this way, so that a thin table design is enabled.

In another embodiment of the invention, in each case separate first and second communication devices are provided for each slot of the patient support and/or each channel of a local coil that can be connected to the at least one slot. It is thus possible to provide a separate pair of communication devices for the first and second data transmission devices for each receive channel that is enabled by the slots. It is preferable, however, to transfer the logically associated data of slots together using a pair of communication devices. In this case the reception channels, which are covered by the respective slot, are then combined to faun an overall data signal.

It is alternatively possible to provide in each case at least one first and one second communication device for data to be transmitted from a number of channels and/or slots. It is therefore possible to already bundle together the data from a number of slots at the patient support side, provided the transmission bandwidth/transmission speed of the communication devices peimits this.

It is expedient for the first and/or second data transmission device to have a converter device for converting data transmitted, or to be transmitted, by the communication devices into optically transmittable data, and vice versa. The converter device can therefore be designed as an optical-electrical converter or coupler. Optical transmission of data, particularly via optical fibers, is not subject to any interferences as a result of the imaging operation, and conversely does not interfere with this imaging operation, so that it is possible to dispense with sheath current filters, as has already been noted. Magnetic resonance reception signals are ideally already digitized on the local coil or slot side and converted into optically transmittable data by a corresponding converter device, so that optical fibers without sheath current filters can be used within the patient support. In the first data transmission device the optically received data can then be converted back and transmitted to the second data transmission device using the at least one data link, wherein the further transfer is preferably also carried out in optical form, and therefore a further converter device is provided. A transmission that is as free of interference as possible is made possible in this way.

In another embodiment of the invention, the connecting device additionally has a first energy transmission device on the patient support side and a second energy transmission device on the docking device side for the wireless inductive and/or capacitive energy transmission from the second energy transmission device to the first energy transmission device. This enables not only the data transmission to be realized wirelessly, but also the energy transmission, so that it is also possible to dispense with all galvanic contacts. To enable the energy transmission, inductively or capacitively coupled energy transmission systems known to those skilled in the art can be used. Because of the rather low powers required on the part of the patient support or the local coils connected to the slots, this is possible without any problems and without producing significant interferences. The energy transmission devices may each include at least one coil for instance, but it should be noted that it is conceivable both to provide just one first energy transmission device and one second energy transmission device in each case. It is also possible to make pairs of energy transmission devices available individually for special slots.

Aside from the connecting device, the invention also concerns a magnetic resonance apparatus comprising at least one patient support with at least one slot for a local coil, a docking device for the patient support, and a connecting device in accordance with the invention as described above.

An inventive patient support for a magnetic resonance apparatus, which can be docked to a docking device at the magnetic resonance apparatus, has at least one slot for a local coil and a first data transmission device, which interacts with a second data transmission device at the docking device, in order to establish a data link in the docked state. The first data transmission device has at least one communication device designed for wireless near field communication with a communication device of the second data transmission device.

The previously described embodiments are applicable to the magnetic resonance apparatus as well as the patient support. A number of patient supports can be provided for a single magnetic resonance apparatus, with the patient supports each having a first data transmission device, which can then interact accordingly with the (one) second data transmission device of the docking device. As part of the data transmission, an item of identification information of a patient support is transmitted to the magnetic resonance apparatus, so that the latter knows which patient support is currently docked.

With an inventive magnetic resonance apparatus or an inventive patient support, the patient support, preferably on the slot side and/or on or in a patient table, can have at least one analog-digital converter for digitizing data to be transmitted via the data link. Furthermore, a converter device for converting the data into optically transmittable data, and if necessary vice versa, can be provided on the slot side so that the data transmission can be carried out optically within the patient support. A converter device of this type is designed as an optical-electronic converter.

It should be noted that the location at which the connecting device is provided can be selected differently. It is preferable for the connecting device, in other words the docking point, to be situated close to the floor, for instance in the region of rollers of a patient support. A support base of the patient support can then remain outside of the patient aperture for instance, while the table is moved therein. Cable connections, which are preferably embodied optically, are then guided by a suitable towing device. In other embodiments, the docking region and thus the connecting device are in the region of the table, for instance the first data transmission device can be integrated in or provided on the table, as discussed above, on top of a support base.

The invention also concerns a method for data transmission between a patient support with at least one slot for a local coil and a docking device of a magnetic resonance apparatus for the patient support, with the data transmission being carried out by near field communication. In the inventive method, all previously described features of the invention can be used correspondingly so that the advantages of the present invention are also achieved with the method.

DESCRIPTION OF THE PREFERRED EMBODIMENTS

Figure 1:
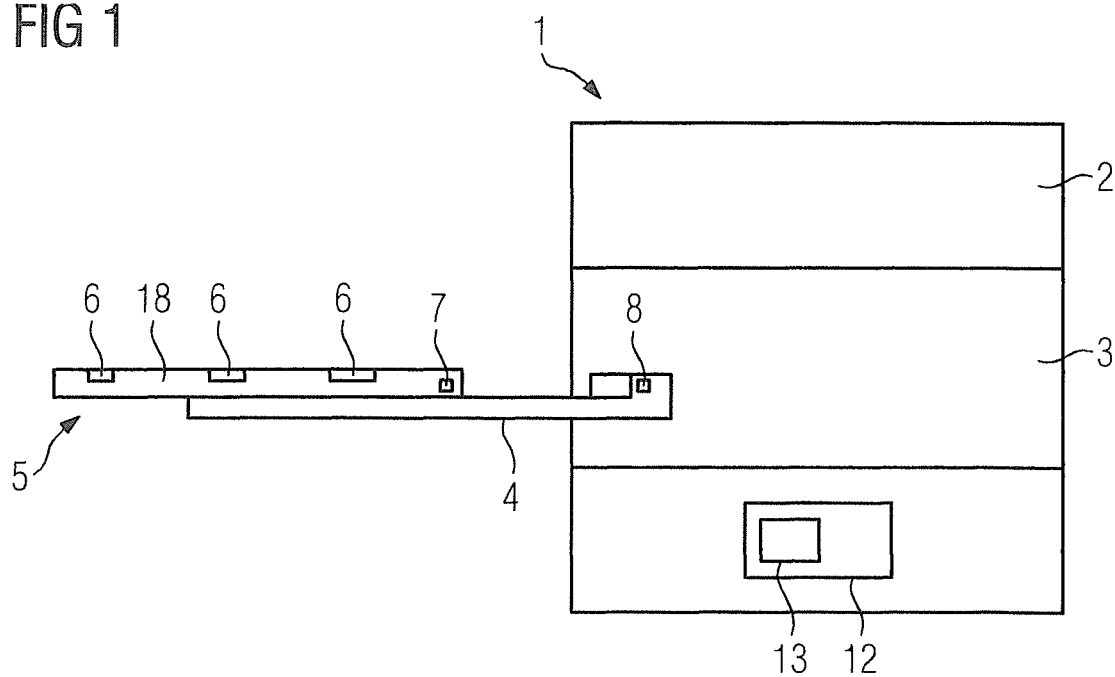
FIG. 1 shows an inventive magnetic resonance apparatus in a first embodiment.

FIG. 1 is a schematic illustration of an inventive magnetic resonance apparatus 1 in a first embodiment in a cross-section. The MR data acquisition scanner 2, as is known, defines a cylindrical patient aperture 3. The basic field magnet, its cooling device, the gradient coil arrangement and the radio frequency coil arrangement are present in the scanner 2, but not for clarity are not shown.

In order to implement magnetic resonance imaging, a patient is to be moved within the patient aperture 3. For this purpose, a patient support 5 can be docked to a docking device 4. For clarity, only the table 18 of the patient support 5 is shown. The patient support 5 has a number of slots 6 for local coils. In order to transmit data or signals from and to the local coils and to ensure a power supply, a wireless connecting device is provided, which has a first data transmission device 7 at the patient support 5 and a second data transmission device 8 at the docking device 4.

Figure 2:
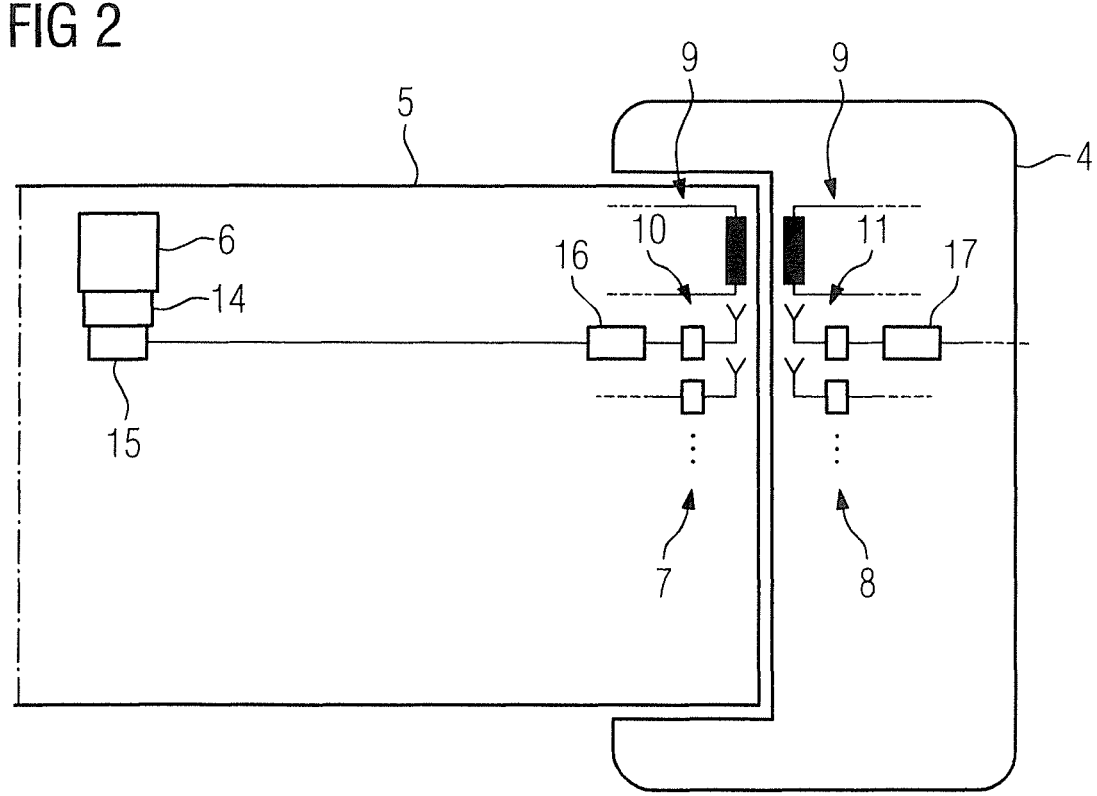
FIG. 2 shows a connecting device of the magnetic resonance apparatus of FIG. 1 in detail.

A more detailed structure is shown in the schematic diagram in FIG. 2, in which a part of the patient support 5 and the docking device 4 can be seen. The connecting device has energy transmission devices 9 operating inductively on the patient support side and on the docking device side in each case, in order to provide power supply to the patient support 5 and for local coils connected to the slots 6. For clarity, the energy lines within the patient support 5 are not shown in more detail.

A first communication device 10 of the first data transmission device 7 and a second communication device 11 of the second data transmission device 8 are assigned on the patient support side and on the docking device side to each slot 6 of the table 18, respectively. The communication devices 10, 11 are each embodied as TransferJet devices and thus serve the near field communication, so a wireless data transmission with a communication range of less than 5 cm is enabled. The communication devices 10, 11 are each designed as transmitting and receiving devices. This means that a data transmission in the faun of control signals from the magnetic resonance apparatus 1 in the direction of the patient support 5 and local coils connected to its slots 6 is possible, as well as in the opposite direction, for instance for transmitting coil information to a control computer 12 (cf. FIG. 1) of the magnetic resonance apparatus 1, or for a transmission of magnetic resonance signals, which were received by a local coil, to a receiving device 13 of the control computer 12 of the magnetic resonance apparatus 1.

Data to be transmitted from a local coil inserted into a slot 6 are first digitized by an analog-digital converter 14, which is integrated into the patient support 5 close to the slots, in the shown embodiment directly adjacent thereto in the table 18. Using a converter device 15 arranged immediately downstream of the analog-digital converter, here an electrical-optical converter, the digital data are thereby converted into data to be transmitted optically. Accordingly a converter device 16 in the form of an optical-electrical converter is present as part of the first data transmission device 7. As part of the second data transmission device 8, a converter devices 17 is present, in order to realize an optical further transfer of data, for instance via optical fibers, which can also be used in the patient support 5. It is possible to largely dispense with sheath current filters.

For simplicity, the specific data lines in FIG. 2 are shown only for one slot 6. Corresponding measures are present for each slot 6.

Figure 3:
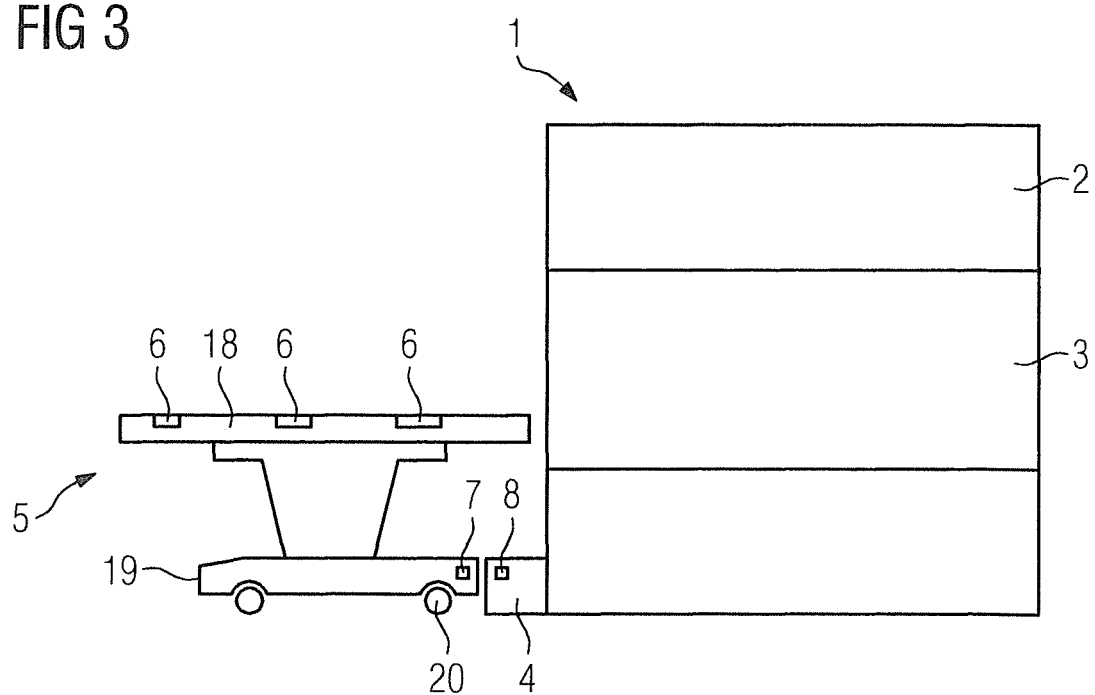
FIG. 3 shows an inventive magnetic resonance apparatus in a second embodiment.

FIG. 3 shows a second, preferred embodiment of an inventive magnetic resonance apparatus 1, wherein the same reference characters are used for the same components. Differing from the first embodiment, the connecting device is realized here close to the floor. The table 18 is supported by a support base 19, which remains outside of the patient aperture 3 in order to receive magnetic resonance data. The first data transmission device 7 is integrated into the support base 19 close to the floor, adjacent to front wheels 20. The second data transmission device 8 is provided in a part of the docking device 4 that projects from the scanner 2. When the patient support 5 is moved toward the docking device 4, the data transmission by near field communication and the energy transmission, as already described in connection with FIG. 2, can be carried out. A cable link between the slots 6 on the table 18 and the support base 19 is realized by a towing device (not shown in more detail).

Because of the overall cable-free embodiment of the connecting device, the demands with respect to the position accuracy on the interface between the patient support 5 and the docking device 4 is reduced. Demands with respect to a number of mating cycles can be easily realized and the interface is not susceptible to soiling since it is designed in a closed manner, as shown. The use of the TransferJet standard functions with low transmitting powers so that image quality is not affected.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A connecting device for establishing a bidirectional data link between a patient support, comprising at least one slot designed to receive a magnetic resonance (MR) local coil therein, and a docking device of an MR apparatus to which the patient support can be docked, said connecting device comprising:
   a first data transmitter at said patient support;
   a second data transmitter at said docking device;
   said first and second data transmitters each being configured as a near field communication (NFC) transmitter and as an NFC receiver, the first and second data transmitters being configured to interact with each other using NFC to establish a bidirectional data link between the patient support and the docking device while the patient support is docked to said docking device;
   a first energy transmitter at said patient support that is separate from the first data transmitter; and
   a second energy transmitter at said docking device that is separate from the second data transmitter, the second energy transmitter wirelessly providing power to the patient support via a transmission of energy from said second energy transmitter to said first energy transmitter,
   wherein said first data transmitter and said second data transmitter are each configured to transmit or receive, via the bidirectional data link, digitized signals identifying a type of local coil inserted into said at least one slot of the patient support, and
   wherein said first and second data transmitters are TransferJet transmitters.

2. A connecting device as claimed in claim 1 wherein said first and second data transmitters are further configured to transmit or receive, via the bidirectional data link, digitized signals including control signals of the MR apparatus to said local coil.

3. A connecting device as claimed in claim 1 wherein said first data transmitter comprises an analog-to-digital converter that converts signals from said local coil into digital signals for transmission via said bidirectional data link.

4. A connecting device as claimed in claim 1 wherein said patient support comprises:
   a plurality of slots, with each slot being designed to individually receive a respective local coil; and
   a plurality of local coil channels respectively associated with said plurality of slots, wherein said first data transmitter is connected to all of said local coil channels and transmits data, via said bidirectional data link, received from all of said local coil channels.

5. A connecting device as claimed in claim 1, wherein said patient support comprises:
   a plurality of slots each designed to individually receive a respective local coil;
   a plurality of local coil channels respectively associated with said plurality of slots; and
   a plurality of first data transmitters respectively individually connected to the respective local coil channels, each of said plurality of first data transmitters communicating via said bidirectional data link with said second data transmitter at said docking device.

6. A connecting device as claimed in claim 1 wherein said patient support comprises:
   a plurality of slots each designed to individually receive a respective local coil;
   a plurality of local coil channels respectively associated with said plurality of slots;
   a plurality of first data transmitters respectively individually connected to the respective local coil channels; and
   a plurality of second data transmitters at said docking device respectively individually communicating with the individual first data transmitters in said plurality of first data transmitters.

7. A connecting device as claimed in claim 1 wherein at least one of said first data transmitter and said second data transmitter comprises a converter that converts data to be transmitted into optically transmittable data, and that converts optical data received via said bidirectional data link into an electrical signal.

8. A connecting device as claimed in claim 5 wherein said first and second energy transmitters are selected from the group consisting of inductive energy transmitters and capacitive energy transmitters.

9. A magnetic resonance (MR) apparatus comprising:
   a patient support comprising at least one slot designed to receive an MR local coil therein;
   a docking device to which the patient support can be docked;
   a first data transmitter at said patient support;
   a second data transmitter at said docking device;
   said first and second data transmitters each being configured as a near field communication (NFC) transmitter and as an NFC receiver, the first and second data transmitters being configured to interact with each other using NFC to establish a bidirectional data link between the patient support and the docking device while the patient support is docked to said docking device;
   a first energy transmitter at said patient support that is separate from the first data transmitter; and
   a second energy transmitter at said docking device that is separate from the second data transmitter, the second energy transmitter wirelessly providing power to the patient support via a transmission of energy from said second energy transmitter to said first energy transmitter,
   wherein said first data transmitter and said second data transmitter are each configured to transmit or receive, via the bidirectional data link, digitized signals identifying a type of local coil inserted into said at least one slot of the patient support, and
   wherein said first and second data transmitters are TransferJet transmitters.

10. A magnetic resonance apparatus as claimed in claim 9 wherein said first and second data transmitters are further configured to transmit or receive, via the bidirectional data link, digitized signals including control signals of the MR apparatus to said local coil.

11. A magnetic resonance apparatus as claimed in claim 10 wherein said first data transmitter comprises an analog-to-digital converter that converts signals from said local coil into digital signals for transmission via said bidirectional data link.

12. A patient support comprising:
a patient-receiving table comprising at least one slot designed to receive a magnetic resonance (MR) local coil therein;
a support based adapted to dock with a docking device of an MR apparatus;
a first data transmitter at said patient-receiving table or at said support base;
said first data transmitter being configured to interact with a second data transmitter at said docking device, each of the first data transmitter and the second data transmitter being configured as a near field communication (NFC) transmitter and as an NFC receiver, the first and second data transmitters being configured to interact with each other using to establish a bidirectional data link between the patient support and the docking device while the patient base is docked to said docking device;
a first energy transmitter that is separate from the first data transmitter; and
a second energy transmitter that is separate from the second data transmitter, the second energy transmitter wirelessly providing power to the patient support or the support via a transmission of energy from said second energy transmitter to said first energy transmitter,
wherein said first data transmitter and said second data transmitter are each configured to transmit or receive, via the bidirectional data link, digitized signals identifying a type of local coil inserted into said at least one slot of the patient support, and
wherein said first and second data transmitters are TransferJet transmitters.

13. A patient support as claimed in claim 12 wherein said first and second transmitters are further configured to transmit or receive, via the bidirectional data link, digitized signals including control signals of the MR apparatus to said local coil.

14. A patient support as claimed in claim 13 wherein said first data transmitter comprises an analog-to-digital converter that converts signals from said local coil into digital signals for transmission via said bidirectional data link.

15. A method for establishing a bidirectional data link between a patient support, comprising at least one slot designed to receive a magnetic resonance (MR) local coil therein, and a docking device of an MR apparatus to which the patient support can be docked, said method comprising:
providing a first data transmitter at said patient support that is configured as a near field communication (NFC) transmitter and as an NFC receiver;
providing a second data transmitter at said docking device that is configured as a NFC transmitter and as an NFC receiver; and
establishing, via an interaction between the first data transmitter and the second data transmitter using NFC, a bidirectional data link between the patient support and the docking device while the patient support is docked to said docking device;
providing a first energy transmitter at said patient support that is separate from the first data transmitter;
providing a second energy transmitter at said docking device that is separate from the second data transmitter; and
wirelessly providing power, via said second energy transmitter, to said patient support via a transmission of energy from said second energy transmitter to said first energy transmitter,
wherein said first data transmitter and said second data transmitter are each configured to transmit or receive, via the bidirectional data link, digitized signals identifying a type of local coil inserted into said at least one slot of the patient support, and
wherein said first and second data transmitters are TransferJet transmitters.

16. A connecting device as claimed in claim 15, wherein the communications provided by the bidirectional data link between the patient support and the docking device further carries control signals from the MR apparatus to the at least one local coil.

* * * * *